United States Patent [19]

Pitet et al.

[11] Patent Number: 4,511,566
[45] Date of Patent: Apr. 16, 1985

[54] 2-N-CYCLOALKYLMETHYL 3-OXO-5,6-DIARYL-as-TRIAZINES

[75] Inventors: Guy Pitet, Toulouse; Henri Cousse; Gilbert Mouzin, both of Castres, all of France

[73] Assignee: Pierre Fabre S.A., Castres, France

[21] Appl. No.: 600,473

[22] Filed: Apr. 16, 1984

[30] Foreign Application Priority Data

Apr. 14, 1983 [FR] France ................. 83 06107

[51] Int. Cl.³ ................. C07D 253/06; C07D 401/04; A61K 31/53
[52] U.S. Cl. ...................... 514/242; 544/182
[58] Field of Search .................. 544/182; 424/249

[56] References Cited

U.S. PATENT DOCUMENTS 4,167,566 9/1979 Pitet et al. ............... 544/182
4,188,387 2/1980 Pitet et al. ............... 544/182

FOREIGN PATENT DOCUMENTS 2368278 5/1978 France .
2383176 10/1978 France .
2478095 9/1981 France .
2500830 9/1982 France .

OTHER PUBLICATIONS

Pitet et al., Estratto do Bollettino Chimico Farmaceutico, vol. 119, pp. 469–482 (1980).

Primary Examiner—John M. Ford
Attorney, Agent, or Firm—Gordon W. Hueschen

[57] ABSTRACT

The present invention concerns new 2-N-cycloalkylmethyl 3-oxo 5,6-diaryl as-triazines, their method of production, pharmaceutical compositions thereof, and their use as medicaments, for treating pain.

The derivatives of 2-N-cycloalkylmethyl 3-oxo 5,6-diaryl as-triazine according to the invention have the general formula I

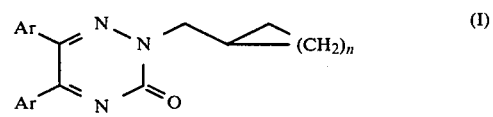

in which
Ar represents a phenyl, furyl, thienyl, or pyridyl group, which group may possibly be substituted by a lower $C_1$ to $C_4$ alkoxy radical, in particular by the methoxy radical, and
n is a whole number having a value of 1 to 4.

14 Claims, No Drawings

2-N-CYCLOALKYLMETHYL 3-OXO 5,6-DIARYL-AS-TRIAZINES

The present invention, developed at the PIERRE FABRE Research Center, relates to new 2-N-cycloalkylmethyl 3-oxo 5,6-diaryl as-triazine derivatives, their method of production, pharmaceutical compositions thereof, and their use as medicaments.

The new chemical compounds which are the object of the present invention have general formula I

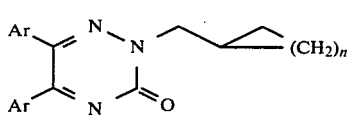

in which:
Ar represents a phenyl, furyl, thienyl or pyridyl group, which groups may possibly be substituted by a lower $C_1$ to $C_4$ alkoxy radical, in particular the methoxy radical and
n is a whole number having a value of 1 to 4, thus including cyclopropyl, cyclobutyl, cyclopentyl, and cyclohexyl compounds.

In the prior art, as illustrated, for instance, by Patents FR-A- No. 2 368 278, No. 2 383 176, No. 2 478 095 and No. 2 500 830 filed in the name of the applicant, it Was shown that the as-triazine compounds had analgesic properties when they were substituted in 2 position on the nitrogen by the following groups:
alkyl, aryl and alkenyl (FR-A- No. 2 368 278)
alkynyl and amino alkyl (FR-A- No. 2 383 176)
ketones and more particularly alkyl C=O alkyl and alkyl —C=O aryl (FR-A- No. 2 478 095)
morpholinoalkyl, dimethylaminoethyl, alkoxyalkyl, alkenoxyalkyl, hydroxyalkyl, acetamido, haloalkyl, dimethylalkyl, N-piperazinoalkyl, diethyl 2-malonyl, alkenylaminoalkyl, nicotinoyloxy 2-ethyl and dihydroxy alkyl (FR-A- No. 2 500 830).

Some of these products furthermore had an interesting antiaggregant component in vitro.

Continuation of the research on this as-triazine structure has made it possible to arrive at the new derivatives which form the object of the present invention.

These compounds differ from Applicant's prior patents by the cycloalkyl nature of the substituent in 2 position on the nitrogen.

It has in fact been found, entirely unexpectedly, that the presence of these cycloalkyl groups and, more particularly, of the 2-cyclopropylmethyl group, confers upon the molecule a very strong analgesic activity and surprisingly increases the duration of action of the product ($ED_{50}$ Writhing Test PBQ 6 hours: $-34\%$), while for the best product of the previous patents the analgesic activity was nil after 2 hours). Finally, in particular, the activity of these new derivatives appears very rapidly in the animal.

Thus, for instance, 2-N-cyclopropylmethyl 3-oxo diparamethoxy 5,6-phenyl as-triazine has a very high anti-aggregating activity.

Inhibition in vitro of the platelet MDA:

$$IC_{50} = 5 \times 10^{-7} M$$

while the most active compound claimed in the previous patents is $$IC_{50} = 5 \times 10^{-5} M.$$

Furthermore, the new compound of the invention is active ex vivo and in vivo, contrary to the compounds of the prior art.

The present invention also concerns the preparation of new derivatives of general formula I. According to the invention, these derivatives are obtained by treating a 3-oxo 5,6-diaryl as-triazine of general formula II:

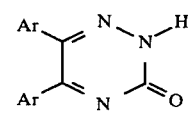

with a sodation agent within an organic solvent and then condensing a methyl cycloalkyl halide of general formula III:

including the methyl cyclopropyl, cyclobutyl, cyclopentyl, and cyclohexyl halides, e.g., the bromides, in which formulas:
Ar and n have the meanings given in claim 1, and
X represents a halogen atom.

In practice, the sodating agent used will generally be an alkali metal hydride, and more particularly sodium hydride.

The initial 3-oxo 5,6-diaryl as-triazines may be synthesized, for instance, by the method described in the aforementioned patents by condensing a diketone (IV) with the semicarbazide (V):

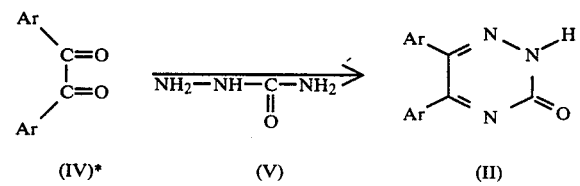

*Starting materials disclosed in the publication of Pitet, Cousse, and Mouzin in Bolletino Chimico Pharmaceutico 119, page 469 (1980) copy, provided herewith.

The invention finally concerns the use of compounds of general Formula I, and more particularly 2-N-cyclopropylmethyl 3-oxo 5,6-diparamethoxy phenyl as-triazine, as medicaments useful in the treatment of stubborn pains and migraines, as well as the pharmaceutical compositions containing them as active principle.

The invention will be described further below in detail with reference to the following non-limitative examples:

EXAMPLE 1

Preparation of 2-N-cyclopropylmethyl 3-oxo 5-6-diparamethoxyphenyl as-triazine (1) Preparation of bromomethyl cyclopropane Reagents:
25 g (0.345 mole) of cyclopropylcarbinol
12 ml (0.125 mole) of $PBr_3$
110 ml of ethyl ether
Manner of Procedure:

25 g of cyclopropylcarbinol are cooled in 100 ml of ether to −70° C., whereupon 12 ml of PBr$_3$ in solution in 110 ml of ethyl ether are added.

The mixture is allowed to return to room temperature and left under strong agitation for 30 minutes.

10 ml of water are added, followed by decantation, washing with water, and drying over sodium sulfate.

The ethyl ether is evaporated slowly at atmospheric pressure. Bromomethylcyclopropane is recovered in quantitative yield. This product has a purity of more than 90% (CPV determination) and it is used crude for the following step.

(2) Preparation of 2-N-cyclopropylmethyl 3-oxo 5-6-diparamethoxy phenyl as-triazine Reagents:
56.15 g (0.18 mole) of 3-oxo 5-6-diparamethoxyphenyl as-triazine
36.15 g (0.27 mole) of 2-bromomethylcyclopropane
7.76 g (0.27 mole) of 80% sodium hydride
900 ml of anhydrous dimethyl acetamide.

Manner of Procedure:
7.76 g of 80% sodium hydride (previously washed with anhydrous ethyl ether) are placed in a 3-liter round-bottom flask provided with mechanical agitation. 900 ml of anhydrous dimethyl acetamide and 56.15 g of 3-oxo 5-6-diparamethoxyphenyl as-triazine are added.

Agitation is effected overnight at room temperature, whereupon 36.15 g of 2-bromomethylcyclopropane are added.

After agitation for 30 minutes, the reaction mixture becomes clear.

The agitation is maintained at room temperature for two hours, whereupon 30 ml of water are added, drop by drop, in order to destroy the excess sodium hydride.

The dimethylacetamide is evaporated under reduced pressure at 70° C., and the residual oil obtained is placed overnight in a refrigerator; it crystallizes out slowly.

The crude crystals are dissolved in ethyl acetate; the organic phase is washed with water and then dried over sodium sulfate and filtered.

The ethyl acetate is evaporated to dryness; the residual oil crystallizes rapidly.

The crystals are triturated in 300 ml of ethyl ether, iced and filtered. 48 g are obtained in a yield of 74% of a product having the formula:

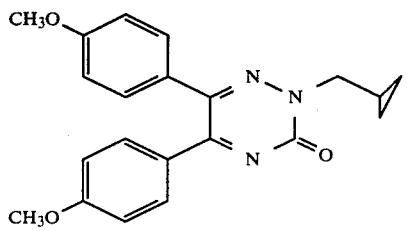

Empirical formula: C$_{21}$H$_{21}$N$_3$O$_3$.
Molecular weight: 363.42.
Crystals: Light yellow.
Melting point: 114° C.
Plate chromatography:
support: silica gel 60 F 254 Merck;
solvent: ethyl acetate/hexane 50:50;
development: UV and iodine;
Rf: 0.37.

IR spectrum (KBr): νcm$^{-1}$ 1670 (C=O); 1610 (C=C aromatic).

NMR spectrum (CDCl$_3$) δppm: 0.5 to 0.8 (m, 4H, CH$_2$ cyclopropanes); 1.5 (m, 1H, CH-cyclopropanes); 3.8 (s, 6H, —OCH$_3$); 4 and 4.1 (d, 2H, CH$_2$-N); 6.7 to 7.6 (m, 8H, aromatic).

UV spectrum (ethanol 95° GL): λmax=246 nm−ε$_M$=18700.

| Elementary Analysis: | C | H | N |
|---|---|---|---|
| % calculated | 69.40 | 5.82 | 11.56 |
| % found | 69.30 | 5.70 | 11.57 |

EXAMPLE 2

Preparation of 2-N-cyclohexylmethyl 3-oxo 5-6-diparamethoxy phenyl as-triazine

In a manner similar to that described in Example 1 but using methyl cyclohexane bromide, there is obtained the product of the formula:

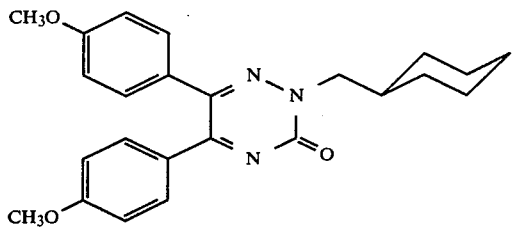

Empirical formula: C$_{24}$H$_{27}$N$_3$O$_3$.
Molecular weight: 405.5.
Crystals: Light yellow.
Melting point: 115° C.
Plate chromatography:
support: silica gel 60 F 254 Merck;
solvent: ethyl acetate/hexane 50:50;
development: UV and iodine;
Rf: 0.49.

EXAMPLE 3

Preparation of 2-N-cyclopropylmethyl 3-oxo 5-6-diorthomethoxyphenyl as triazine

In a manner similar to that described in Example 1 but using 2-2'-dimethoxy benzil*, there is obtained the product of the formula:

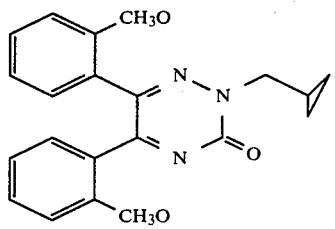

\* obtained by condensation of 2-methoxybenzaldehyde with itself and oxidation of the intermediate benzoin, and thereafter condensed with the semicarbazide according to the foregoing reaction sequence.

Empirical formula: C$_{21}$H$_{21}$N$_3$O$_3$.
Molecular weight: 363.4.
Crystals: Pale yellow.

Melting point: 150° C.
Plate chromatography:
support: silica gel 60 F 254 Merck;
solvent: ethyl acetate/petroleum ether 50:50;
development: UV and iodine;
Rf: 0.38.

EXAMPLE 4

2-N-cyclopropylmethyl 3-oxo 5-6-diorthofurfuryl as-triazine

Operating under the same conditions as in Example 1 but starting with 3-oxo 5-6-diorthofurfuryl as-triazine*, there is obtained the derivative of the formula:

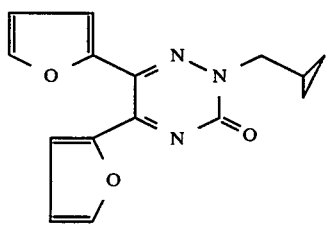

* obtained according to the reaction sequence starting from 2-furfuraldehyde.

Empirical formula: $C_{15}H_{13}N_3O_3$.
Molecular weight: 238.28.
Crystals: Light brown.
Melting point: 128° C.
Plate chromatography:
support: silica gel 60 F 254 Merck;
solvent: ethyl acetate/hexane 50:50;
development: UV and iodine;
Rf: 0.40.

EXAMPLE 5

2-N-cyclopropylmethyl 3-oxo 5-6-diorthothienyl as-triazine

Operating under the same conditions as in Example 1 but starting with 3-oxo 5-6-diorthothienyl as-triazine*, there is obtained the derivative of the formula:

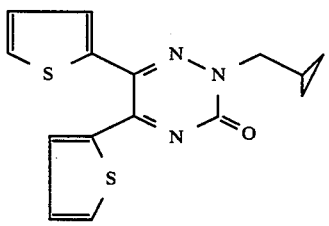

* obtained starting from 2-thienaldehyde.

EXAMPLE 6

2-N-cyclopropylmethyl 3-oxo 5-6-diorthopyridyl as-triazine

Operating under the same conditions as in Example 1 but starting with 3-oxo 5-6-diorthopyridyl as-triazine* there is obtained the derivative of the formula:

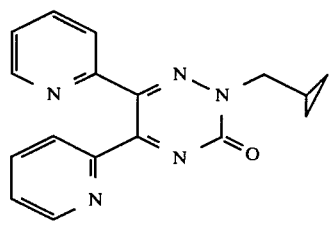

* obtained starting from 2-pyridinaldehyde.

EXPERIMENTS

The compounds of the invention, and especially 2-N-cyclopropylmethyl 3-oxo 5-6-diparamethoxyphenyl as-triazine, have been the object of toxicological, pharmacological, and clinical tests which have made it possible to demonstrate remarkable analgesic and anti-aggregating properties.

(a) Toxicology

The toxicity study was carried out on the conventional mouse, weighing about 20 g.

The substance was administered orally and intraperitoneally. The median lethal doses were calculated by the method of MILLER and TAINTER—Proc. Soc. Exper. Biol. Med. 1944, 57, 261. They were respectively >1500 mg/kg per os and >500 mg/kg intraperitoneally.

(b) Pharmacological Properties (1) Analgesic Properties

The activity on the phenylbenzoquinone writhing test (according to SIEGMUND et al.—J. Pharm. Expt. Ther. 1957, 119, 453) was determined after administration of the product per os.

The $ED_{50}$ of the product is 1.4 mg/kg.

The kinetics of action of the product at 3 mg/kg per os is set forth in the following table:

| Time | % Decrease in writhing |
| --- | --- |
| 5 minutes | −78% |
| 30 minutes | −62% |
| 1 hour | −41% |
| 2 hours | −35% |
| 6 hours | −34% |

(2) Anti-aggregating Properties

In vitro

On the inhibition test in vitro on the platelet MDA the product has an $IC_{50}$ of $5.10^{-7}M$.

Ex vivo

In this test carried out ex vivo the product has an $ED_{50}$ of 1.5 mg/kg.

In vivo

In a 4-day test, the product produces total inhibition with respect to arachidonic acid in a dose of $5.10^{-6}M$.

(c) Therapeutic Applications

2-N-cyclopropylmethyl 3-oxo 5-6-diparamethoxy phenyl as-triazine is slightly colored; it is definitely better tolerated upon repeated administration than the molecules described in the prior art.

In view of their perfect tolerance and remarkable pharmacological properties, the chemical compounds which are the object of the invention can be used for the treatment of stubborn pains which respond to prolonged treatment.

The results have also proven satisfactory in the case of the treatment of migraine disturbances.

The pharmaceutical preparations containing this active principle can be administered orally, parenterally or rectally. These pharmaceutical compositions may also contain, in combination, other pharmaceutically and therapeutically acceptable active principles.

The unit dose will, for instance, be between about 10 and about 100 mg.

The following examples of pharmaceutical preparations containing an active principle forming the object of the present invention are given simply by way of illustration:

| | |
|---|---|
| (a) Tablets | |
| 2-N—cyclopropylmethyl 3-oxo 5-6-diparamethoxyphenyl as-triazine | 15 mg |
| Excipient: lactose | |
| (b) Capsules | |
| 2-N—cyclopropylmethyl 3-oxo 5-6-diparamethoxyphenyl as-triazine | 30 mg |
| (c) Suppositories, adults | |
| 2-N—cyclopropylmethyl 3-oxo 5-6-diparamethoxyphenyl as-triazine | 50 mg |
| Semi-synthetic glycerides q.s.p. | 1 suppository of 1 g |

As will be noted, the compositions of (a) and (c) comprise the usual pharmaceutically-acceptable carrier, whereas (b) encapsulates the active ingredient per se. For treatment of a subject suffering from pain, including headache, a compound of the invention is administered orally or parenterally in an effective pain-relieving amount, either alone or in the form of a pharmaceutical composition thereof.

In conclusion, from the foregoing, it is apparent that the present invention provides novel compounds, which are useful analgesics for the relief of pain, pharmaceutical compositions thereof, and a method of treating pain therewith, all having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. 2-N-cycloalkylmethyl 3-oxo 5-6-diaryl as-triazine having the formula in which:
Ar represents phenyl, furyl, thienyl, or pyridyl, which may be substituted by a lower $C_1$ to $C_4$ alkoxy radical, and
n is a whole number having a value of 1 to 4.

2. Compound of claim 1 wherein Ar represents methoxyphenyl.

3. Compound of claim 1 which is 2-N-cyclopropylmethyl 3-oxo 5-6-diparamethoxy phenyl as-triazine.

4. Compound of claim 1 which is 2-N-cyclohexylmethyl 3-oxo 5-6-diparamethoxy phenyl as-triazine.

5. Compound of claim 1 which is 2-N-cyclopropylmethyl 3-oxo 5-6-diorthomethoxy phenyl as-triazine.

6. Compound of claim 1 which is 2-N-cyclopropylmethyl 3-oxo 5-6-diorthofurfuryl as-triazine.

7. Compound of claim 1 which is 2-N-cyclopropylmethyl 3-oxo 5-6-diorthothienyl as-triazine.

8. Compound of claim 1 which is 2-N-cyclopropylmethyl 3-oxo 5-6-diorthopyridyl as-triazine.

9. A pharmaceutical composition useful for treating pain which contains an effective pain-relieving amount of at least one compound according to claim 1 together with a pharmaceutically-acceptable carrier.

10. A pharmaceutical composition useful for treating pain which contains an effective pain-relieving amount of at least one compound according to claim 2 together with a pharmaceutically-acceptable carrier.

11. The pharmaceutical composition according to claim 9 wherein the compound is 2-N-cyclopropylmethyl 3-oxo 5-6-diparamethoxyphenyl as-triazine.

12. The method of relieving pain in a subject afflicted therewith which comprises the step of administering an effective pain-relieving amount of a compound of claim 1 to the said subject.

13. The method of relieving pain in a subject afflicted therewith which comprises the step of administering an effective pain-relieving amount of a compound of claim 2 to the said subject.

14. The method of claim 12, wherein the compound is 2-N-cyclopropylmethyl 3-oxo 5-6-diparamethoxyphenyl as-triazine.

* * * * *

UNITED STATES PATENT AND TRADEMARK OFFICE
CERTIFICATE OF CORRECTION

PATENT NO. : 4,511,566

DATED : April 16, 1985

INVENTOR(S) : Guy Pitet, Henri Cousse and Gilbert Mouzin

It is certified that error appears in the above-identified patent and that said Letters Patent is hereby corrected as shown below:

Col. 4, lines 54 and 61; "$CH_3O$" (both occurrences) should read -- $OCH_3$ -- (both occurrences)

Signed and Sealed this

Twenty-second Day of October 1985

[SEAL]

Attest:

DONALD J. QUIGG

Attesting Officer

Commissioner of Patents and Trademarks—Designate